(12) United States Patent
Willoughby et al.

(10) Patent No.: US 11,759,567 B2
(45) Date of Patent: Sep. 19, 2023

(54) MEDICAMENT DELIVERY DEVICE WITH A REMOVABLE CAP AND LOCKING MEMBER FOR PREVENTING ACCIDENTAL ACTIVATION

(71) Applicant: SHL MEDICAL AG, Zug (CH)

(72) Inventors: Alastair Willoughby, Cambridgeshire (GB); George Savell, Dry Drayton (GB); Donald Steel, London (GB)

(73) Assignee: SHL MEDICAL AG, Zug (CH)

( * ) Notice: Subject to any disclaimer, the term of this patent is extended or adjusted under 35 U.S.C. 154(b) by 570 days.

(21) Appl. No.: 16/961,025

(22) PCT Filed: Jan. 17, 2019

(86) PCT No.: PCT/GB2019/050120
§ 371 (c)(1),
(2) Date: Jul. 9, 2020

(87) PCT Pub. No.: WO2019/141985
PCT Pub. Date: Jul. 25, 2019

(65) Prior Publication Data
US 2021/0060251 A1    Mar. 4, 2021

(30) Foreign Application Priority Data
Jan. 19, 2018  (GB) ...................... 1800902

(51) Int. Cl.
*A61M 5/20* (2006.01)
*A61M 5/24* (2006.01)
*A61M 5/32* (2006.01)

(52) U.S. Cl.
CPC ............ *A61M 5/20* (2013.01); *A61M 5/2033* (2013.01); *A61M 5/2046* (2013.01); *A61M 5/24* (2013.01);
(Continued)

(58) Field of Classification Search
CPC .... A61M 5/20; A61M 5/2033; A61M 5/2046; A61M 5/24; A61M 5/3202; A61M 2005/2073; A61M 5/31571
See application file for complete search history.

(56) References Cited

U.S. PATENT DOCUMENTS 4,946,069 A      8/1990  Fuchs
2015/0174325 A1*  6/2015  Young ................. A61M 5/2033
                                                  604/135
(Continued)

FOREIGN PATENT DOCUMENTS

EP          0311863 A2    4/1989
JP       2017-508548 A    3/2017
(Continued)

OTHER PUBLICATIONS

From the ISA: International Search Report and Written Opinion of the ISA; dated Apr. 10, 2019; pp. 1-14.
(Continued)

*Primary Examiner* — Amber R Stiles
*Assistant Examiner* — Nelson Louis Alvarado, Jr.
(74) *Attorney, Agent, or Firm* — MCDONNELL BOEHNEN HULBERT & BERGHOFF LLP (57) ABSTRACT

A medicament delivery device including a housing for receiving a syringe, the housing having first and second casing parts separably attachable to one another. The device further includes a sleeve receivable within the housing and including a tubular wall having an inner surface delimiting a bore and an opposing outer surface. A locking member is receivable within the second casing part such that the locking member is axially movable between first and second axial positions relative to the second casing part. In the first axial position the locking member is engageable with the outer surface to inhibit an axial movement of the sleeve relative to the first casing part. In the second axial position
(Continued)

the locking member is disengageable from the outer surface. The device, in one or more embodiments, includes an application as an autoinjector.

21 Claims, 9 Drawing Sheets

(52) U.S. Cl.
CPC ... *A61M 5/3202* (2013.01); *A61M 2005/2073* (2013.01)

(56) References Cited

U.S. PATENT DOCUMENTS

| | | | |
|---|---|---|---|
| 2016/0263323 A1* | 9/2016 | Koppelman | A61M 5/3148 |
| 2016/0325044 A1 | 11/2016 | Tschirren et al. | |
| 2017/0144200 A1 | 5/2017 | Whinnem et al. | |

FOREIGN PATENT DOCUMENTS

| | | |
|---|---|---|
| WO | 2014009705 A1 | 1/2014 |
| WO | 2015/144871 A1 | 10/2015 |
| WO | 2017/046556 A1 | 3/2017 |
| WO | 2017/089281 A1 | 6/2017 |
| WO | 2017144200 A1 | 8/2017 |
| WO | 2018011417 A1 | 1/2018 |

OTHER PUBLICATIONS

From the International Searching Authority—"Notification of Transmittal of the International Search Report and The Written Opinion of the International Searching Authority, or the Declaration"; dated Oct. 4, 2019; pp. 1-14.

From the Intellectual Property Office—"Combined Search and Examination Report under Sections 17 & 18(3)"; Date of Report: dated Jun. 29, 2018; pp. 1-3.

Intellectual Property Patent Office, Government of India; Examination Report of corresponding application No. 202037026092, filed Jun. 20, 2020; Date of Report: dated May 17, 2022; pp. 1-6.

European Examination Report, European Patent Office, European Patent Application No. 19701712.2, dated May 27, 2021, 5 pages.

\* cited by examiner

MEDICAMENT DELIVERY DEVICE WITH A REMOVABLE CAP AND LOCKING MEMBER FOR PREVENTING ACCIDENTAL ACTIVATION

This application is a U.S. national stage application under 35 U.S.C. § 371 of PCT International Application Serial No. PCT/GB2019/050120 which has an international filing date of Jan. 17, 2019, designates the United States of America, and claims the benefit of GB Application No. 1800902.7, which was filed on Jan. 19, 2018. The disclosures of each of these prior applications are hereby expressly incorporated by reference in their entirety.

TECHNICAL FIELD

The invention relates to a medicament delivery device, particularly to an automatically actuable syringe.

BACKGROUND

Automatically actuable syringes, sometimes referred to as autoinjectors, are well known. These devices include a power source, such as a compressed spring or a container of propellant, to deliver a dose of medicament to a patient. Further components may include a needle shield for selectively covering a needle of the device during storage and various stages of delivery. As the skilled reader will understand, the needle shield may often serve to actuate the device by displacing internal components of the device rearwardly upon a user pressing the device against an injection site in order to release a compressed spring or open a container of propellant. However, in the event that the device is dropped onto a hard surface, the internal components may be displaced rearwardly by inertia such that the device is unintentionally actuated. Clearly, there is a desire to inhibit unintentional actuation to maintain the efficacy of the device. It is an object of embodiments of the invention to at least reduce a problem associated with one or more known arrangements.

SUMMARY OF THE INVENTION

According to an aspect of the invention, there is provided a medicament delivery device comprising: a housing for receiving a syringe, the housing having first and second casing parts separably attachable to one another; a sleeve receivable within the housing and comprising a tubular wall having an inner surface delimiting a bore and an opposing outer surface; and a locking member receivable within the second casing part such that the locking member is axially movable between first and second axial positions relative to the second casing part, wherein in the first axial position the locking member is engageable with the outer surface to inhibit an axial movement of the sleeve relative to the first casing part and in the second axial position the locking member is disengageable from the outer surface. As such, the locking member may selectively maintain a relative position of the housing to the sleeve. Of course, the locking member may be disengageable from the outer surface to permit the axial movement of the sleeve. By engaging with the outer surface, the locking member may not obstruct, or not extend into, the bore of the device.

In certain embodiments, the medicament delivery device may be actuable by, i.e. as a direct consequence of, the axial movement of the sleeve. As such, the locking member may reduce the likelihood of unintentional actuation of the device. The axial movement may be a rearward movement. The locking member may be moveable from the first axial position to the second axial position by separation of the first and second casing parts from one another.

Optionally, the locking member may be engageable with the outer surface in that the locking member may comprise a body portion having one or more radially inward protrusions extending therefrom engageable with the outer surface. The body portion may be an annular body portion. The body portion may be circumferentially continuous or discontinuous. In certain embodiments, the body portion may delimit an opening through which the sleeve is receivable, either partially or wholly. As such, the locking member, or at least a portion thereof, may be receivable concentrically between the sleeve and the second casing part.

The locking member may be engageable with the outer surface in that the outer surface may have a radially inward groove extending therealong, i.e. around a periphery of the sleeve, in which the one or more radially inward protrusions may be engageable. The radially inward groove may be circumferentially continuous or discontinuous. The groove may enable engagement of the one or more radially inward protrusions with the outer surface in any rotational orientation of the sleeve relative to the locking member.

In certain embodiments, the body portion may have one or more first axially extending arms, proximate a free end of which a respective one of the one or more radially inward protrusions may be integral or coupled to. A plurality of the first axially extending arms may be equispaced about the body portion.

The locking member may be disengageable from the outer surface by a radially outward movement of the one or more radially inward protrusions. The radially outward movement of the one or more radially inward protrusions may be by deformation, for example resilient deformation, of the locking ring. More specifically, the radially outward movement of the one or more radially inward protrusions may be by deformation, for example resilient deformation, of the one or more first axially extending arms.

In certain embodiments, in the first axial position the radially outward movement of the one or more radially inward protrusions may be inhibited by abutment of the locking member against the second casing part. More specifically, the radially outward movement of the one or more radially inward protrusions may be inhibited by abutment of the locking member against a first radially inwardly extending region of the second casing part. The first radially inwardly extending region may comprise one or more first bumps, ridges and/or ribs extending over a first portion of the second casing part.

In the first axial position the first radially inwardly extending region may be radially aligned with the one or more radially inward protrusions and in the second axial position the first radially inwardly extending region may not be radially aligned with the one or more radially inward protrusions. As such, in the second axial position, a space may be provided to accommodate deflection of the locking member. The locking member may be disengageable from the outer surface by separation of the first and second casing parts from one another.

Optionally, the body portion may have one or more radially outward protrusions extending therefrom engageable with the second casing part to retain the locking member within the second casing part. The body portion may have one or more second axially extending arms, proximate a free end of which a respective one of the one or more radially outward protrusions is integral or coupled to.

The one or more radially outward protrusions may be engageable with the second casing part by abutment of the one or more radially outward protrusions against a second radially inwardly extending region of the second casing part. The second radially inwardly extending region may comprise one or more second bumps, ridges and/or ribs extending over a second portion of the second casing part.

In certain embodiments, the second casing part may comprise a cap separably attachable to the first casing part at an end of the medicament delivery device. Additionally, or alternatively, the sleeve may comprise a needle guard to selectively cover a needle of the medicament delivery device. The second casing part may comprise or is coupled to a needle sheath remover receivable within the bore. The first and second casing parts may be separably attachable to one another in that the first and second casing parts form one of a push fit, a snap fit and a screw fit with one another.

In certain embodiments, the medicament delivery device may further comprise a power source provided as a propellant. The propellant may be a liquefied gas propellant. The power source may comprise a propellant that includes a hydrofluoroalkane ("HFA"). Additionally, or alternatively, the power source may comprise a propellant that includes a hydrofluoroolefin ("HFO"). In certain embodiments, the medicament delivery device may comprise a power source provided as a compression spring.

According to a further aspect of the invention, there is provided a medicament delivery device comprising: a housing for receiving a syringe, the housing having first and second casing parts separably attachable to one another; an actuator member receivable within the housing and comprising a tubular wall having an inner surface delimiting a bore and an opposing outer surface, the medicament delivery device being actuable by an actuating movement of the actuator member relative to the first casing part; and a locking member receivable within the second casing part such that the locking member is axially movable between first and second axial positions relative to the second casing part, wherein in the first axial position the locking member is engageable with the outer surface to inhibit the actuating movement and in the second axial position the locking member is disengageable from the outer surface.

As the skilled reader will understand, features described above with reference to the first aspect of the invention may be combined with features of the further aspect of the invention.

BRIEF DESCRIPTION OF THE DRAWINGS

Embodiments of the invention will now be described, by way of example only, with reference to the accompanying figures, in which.

DETAILED DESCRIPTION

Figure 1:
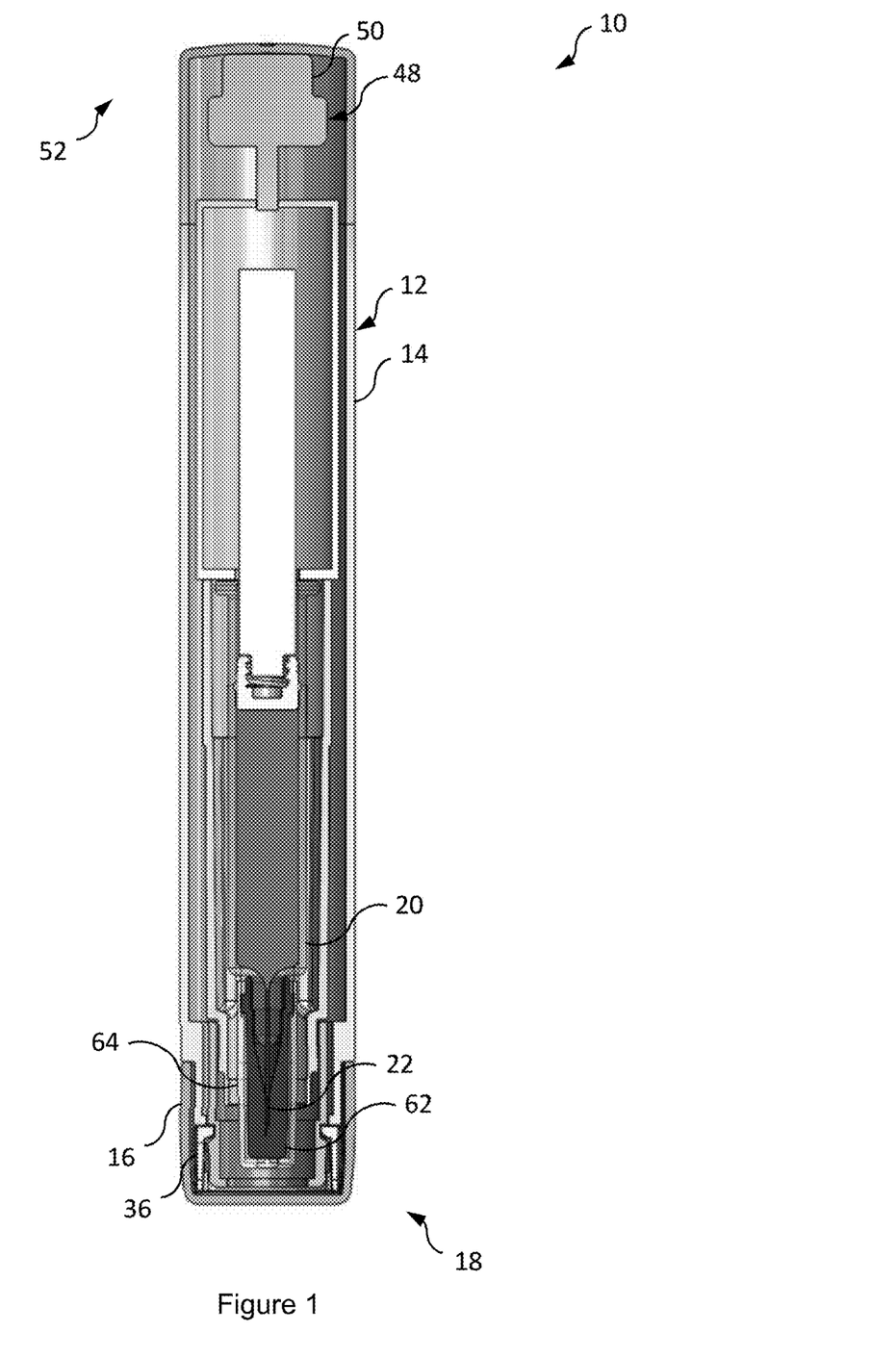
FIG. 1 is a cross-sectional view of a medicament delivery device according to an embodiment of the invention.
Figure 2:
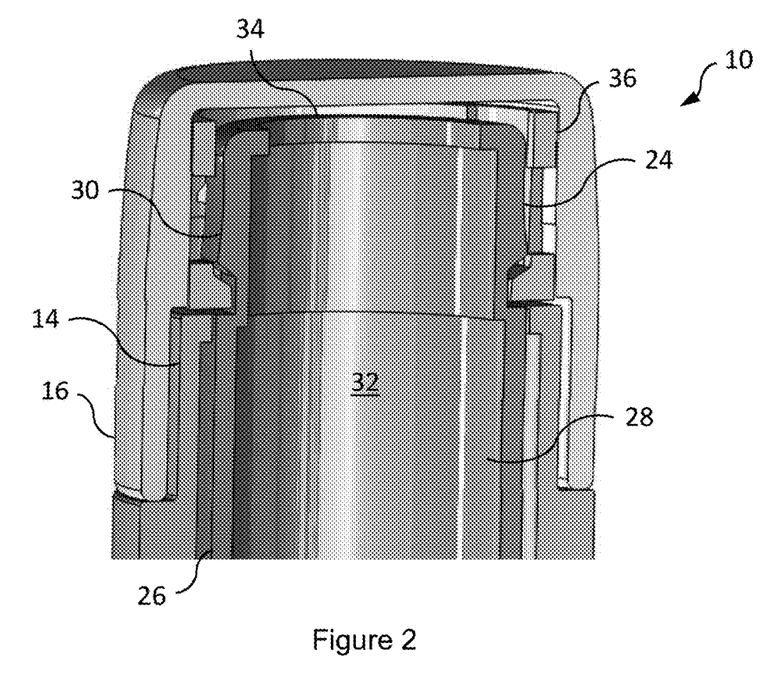
FIG. 2 is a perspective cross-sectional view of a proximal end of the medicament delivery device of FIG. 1.

FIG. 1 shows a medicament delivery device 10 according to an embodiment of the invention. The device 10 has particular application as an autoinjector. The device 10 comprises a housing 12 having a first casing part 14 and a second casing part 16. The first and second casing parts 14, 16 are separably attachable to one another, for example by push fit engagement. As shown in the illustrated embodiment, the second casing part 16 may be an end cap separably attachable to the first casing part 14 at a proximal end 18 of the device 10. The housing 12 is configured to receive a syringe 20 having a needle 22. The syringe 20 may be movable within the housing 12 to deliver a dose of medicament to a patient. The device 10 further includes a sleeve 24 (best shown in FIG. 2) receivable within the housing 12 such that the sleeve 24 is axially moveable relative to the first casing part 14. The sleeve 24 comprises tubular wall 26 having an inner surface 28 and an outer surface 30. The inner surface 28 bounds, i.e. delimits, a bore 32, in which the needle 20 may be receivable. The bore 32 may have an open end 34, through which, in use, the needle 20 may selectively pass to deliver the dose of medicament. As such, the sleeve 24 may comprise, or serve as, a needle guard. Thus, the sleeve 24 may reduce the likelihood of needle-stick injuries and/or inhibit the undesirable re-use of the device 10. While the sleeve 24 is shown in the accompanying figures to be cylindrical, other shapes are contemplated, for example elliptical or rectangular. Moreover, the sleeve 24 may be circumferentially continuous or circumferentially discontinuous.

In certain embodiments, the sleeve 24 may be axially moveable relative to the first casing part 14 to actuate the device 10, i.e. to release a power source 48 to drive delivery of the dose of medicament. In certain embodiments, the power source 48 may comprise a compression spring (not shown). In certain embodiments, the power source 48 may comprise a container 50 of propellant. The propellant may comprise a liquefied gas propellant that vaporises to provide a vapour pressure. Prior to use, the propellant may be contained in the container 50 at a distal end 52 of the device 10. Axial movement of the sleeve 24 may compress the container 50 to vent the propellant and thus drive delivery of the dose of medicament. As the skilled reader will understand, the propellant may be or comprise any suitable propellant. However, in certain embodiments, the propellant may be or comprise a hydrofluoroalkane ("HFA"), e.g. HFA 341a, HFA227, HFA 422D, HFA 507, or HFA 410A. In certain embodiments, the propellant may be or contain a hydrofluoroolefin ("HFO"), e.g. HFO 1234yf or HFO 1234ze.

Figure 3:
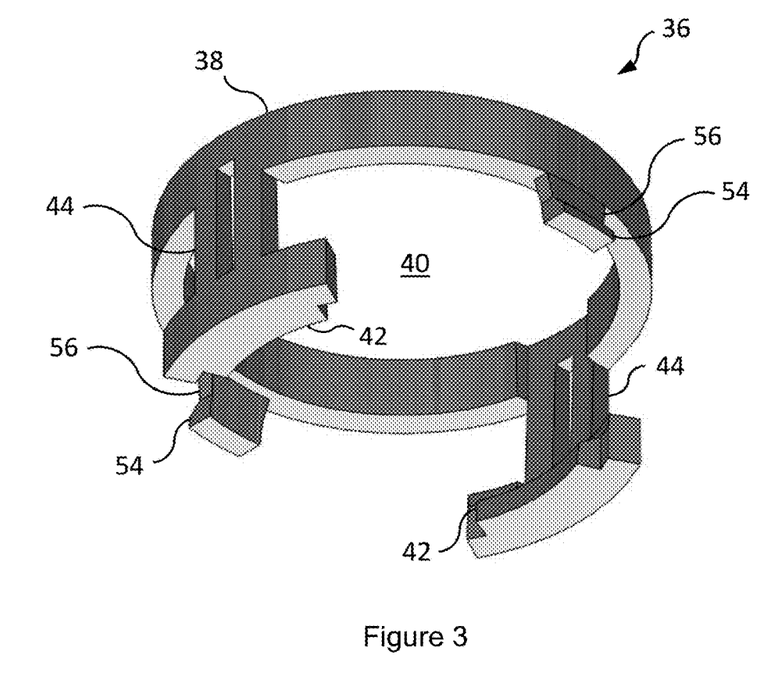
FIG. 3 is a perspective view of a locking member of the medicament delivery device of FIG. 1.

The device 10 further comprises a locking member 36 (best shown in FIG. 3). As shown in the illustrated embodiment, the locking member 36 may comprise an annular body portion 38. Although, non-annular configurations are envisaged. The annular body portion 38 may be circumferentially continuous, at least over an axial length thereof. As such, the annular body portion 38 may delimit an opening 40 extending axially therethrough. The annular body portion 38 may have one or more radially inward protrusions 42 extending therefrom. In certain embodiments, the radially inward protrusions 42 may comprise a diametrically opposed pair of the radially inward protrusions 42. Thus, the radially inward protrusions 42 may be equispaced about the annular body portion 38, although such equispacing may also be achieved with three or more of the radially inward protrusions 42. The annular body portion 38 may have one or more first axially ending arms 44, upon which a respective one of the radially inward protrusions 42 may be integral or coupled to. Each of the radially inward protrusions 42 may be proximate a free end of each of the first axially ending arms 44. Additionally, or alternatively, the annular body portion 38 may have one or more radially outward protrusions 54 extending therefrom. The annular body portion 38 may have one or more second axially ending arms 56, upon which a respective one of the radially outward protrusions 54 may be integral or coupled to. Each of the radially outward protrusions 54 may be proximate a free end of each of the second axially ending arms 56. The radially outward protrusions 54 may be equispaced about the annular body portion 38, although such equispacing may also be achieved with three or more of the radially outward protrusions 54.

Figure 4A:
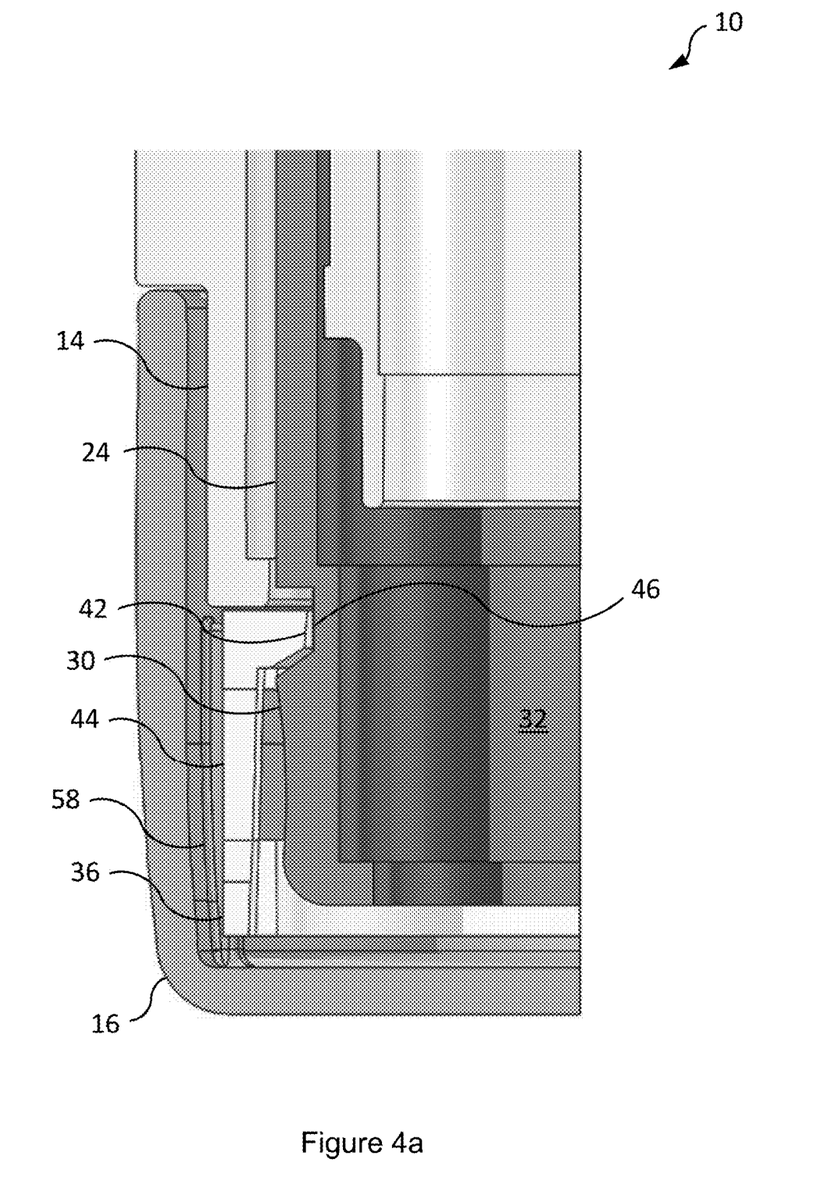
FIGS. 4A and 4B are partial cross-sectional views of the proximal end of the medicament delivery device of FIG. 1, in which the locking member is in a first axial position.
Figure 4B:
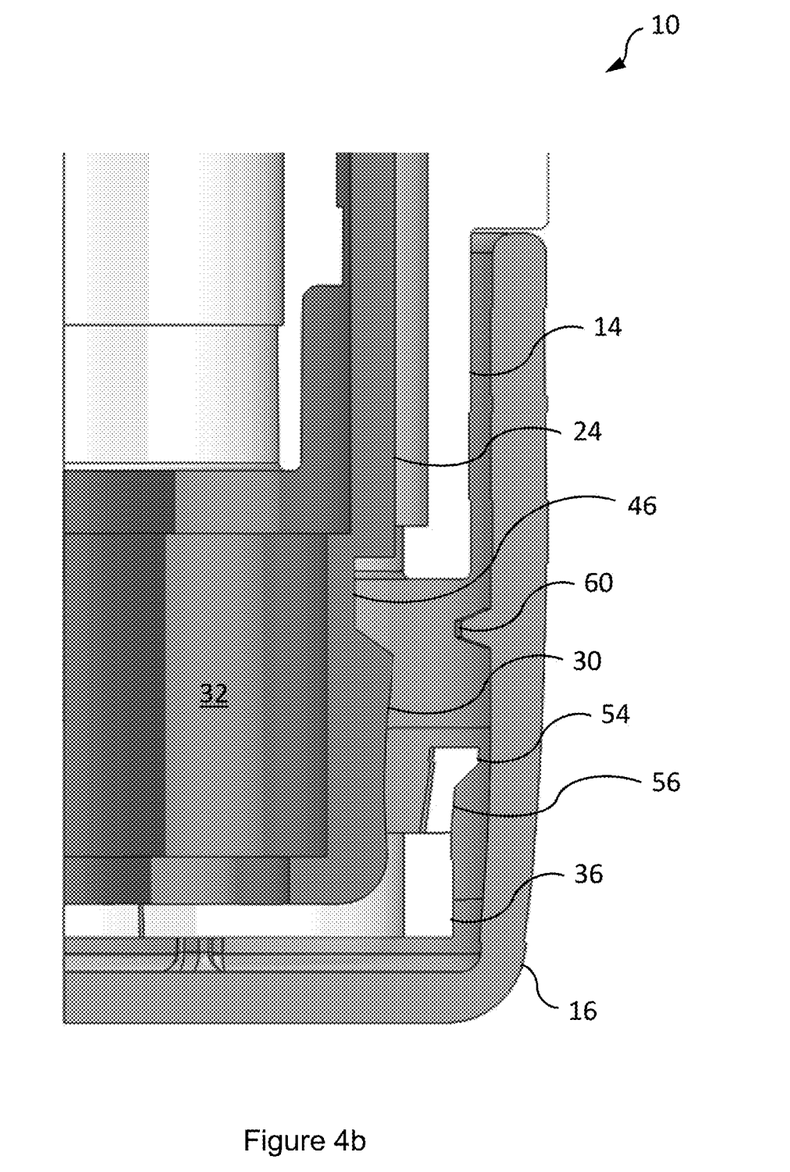

The locking member 36 is receivable within the second casing part 16 such that the locking member 36 is moveable between first and second axial positions, relative to the second casing part 16, i.e. the locking member is axially slidable within the second casing part 16. The first axial position is best shown in FIGS. 4A and 4B, which are offset by 90° from one another, to show different features of the device 10. The second axial position is best shown in FIGS. 5A, 5B, 6A and 6B, which are similarly offset by 90° to one another. Crucially, in the first axial position, the locking member 36 is engageable with the outer surface 30 of the sleeve 24 to inhibit an axial movement of the sleeve 24 relative to the first casing part 14. The axial movement may be a rearward movement. In the illustrated embodiment, engagement of the locking member 36 with the outer surface 30 is achieved by the radially inward protrusions 42 being receivable within a groove 46 of the outer surface 30. The groove 46 provides an abutment surface against which the locking member 36 may abut to interrupt an axial path of the sleeve 24. The groove 46 may extend radially inwardly along the outer surface 30 about a circumference of the sleeve 24, either partially or wholly. However, in certain embodiments, engagement of the locking member 36 with the outer surface 30 may be alternatively achieved, for example the outer surface 30 may comprise a radially outward ridge receivable within a groove of the locking member 36.

The locking member 36 may be disengageable from the outer surface 30 by a radially outward movement of the radially inward protrusions 42. In certain embodiments, the radially outward movement may remove the radially inward protrusions 42 from the groove 46. The radially outward movement may be by deformation of the locking ring 36, for example resilient deformation of the locking ring 36. More specifically, the radially outward movement may be by deformation of the first axially extending arms 44, upon which the radially inward protrusions 42 may be integral or coupled to.

Prior to use of the device 10, the locking member 36 may be in the first axial position. In the first axial position, the locking member 36 may be substantially non-deformed, i.e. the locking member 36 may be in a free state, with the first and second casing parts 14, 16 attached to one another. As such, in the first axial position, the locking member 36 may be receivable concentrically between the second casing part 16 and the outer wall 30 of the sleeve 24, as shown in FIGS. 4A and 4B. In the first axial position, the locking member 36 cannot disengage from the outer surface 30. This is because the outward movement of the radially inward protrusions 42 may be inhibited by abutment of the locking member 36 against the second casing part 16 (i.e. in the first axial position, there is no space available radially outward of the locking member 36 to accommodate the radially outward movement). To this end, the second casing part 16 may comprise a first radially inwardly extending region 58, against which the locking member 36 may abut to inhibit the outward movement of the radially inward protrusions 42. As shown in the illustrated embodiment, the first radially inwardly extending region 58 may comprise one or more ribs. Additionally, or alternatively, the first radially inwardly extending region 58 may comprise an annular ridge, and/or one or more bumps.

In the event that the device 10 is dropped, or struck, on the distal end 52, inertia of the sleeve 24, and/or of other components of the device 10 to which the sleeve 24 may be coupled to, may urge the sleeve 24 to move axially rearwardly. The rearward axial movement of the sleeve 24 relative to the first casing part 14 may actuate the device 10. In certain embodiments, the rearward axial movement of the sleeve 24 may alternatively prime the device 10 or undesirably misalign various components of the device 10. However, the axial movement of the sleeve 24 relative to the first casing part 14 may be inhibited by axial abutment of the sleeve 24 against the locking member 36, as the radially inward protrusions 42 may interrupt, or block, the axial path of the sleeve 24. Consequently, a load may be transferred from the sleeve 24 to the locking member 36, which may be subsequently transferred from the locking member 36 to the first casing part 14. In other words, the sleeve 24 may be axially supported by the locking member 36 and the locking member 36 may be supported by the first casing part 14. The first casing part 14 may be sufficiently stiff to absorb the impact of the device 10 being dropped, for example on the floor, or struck.

Figure 5A:
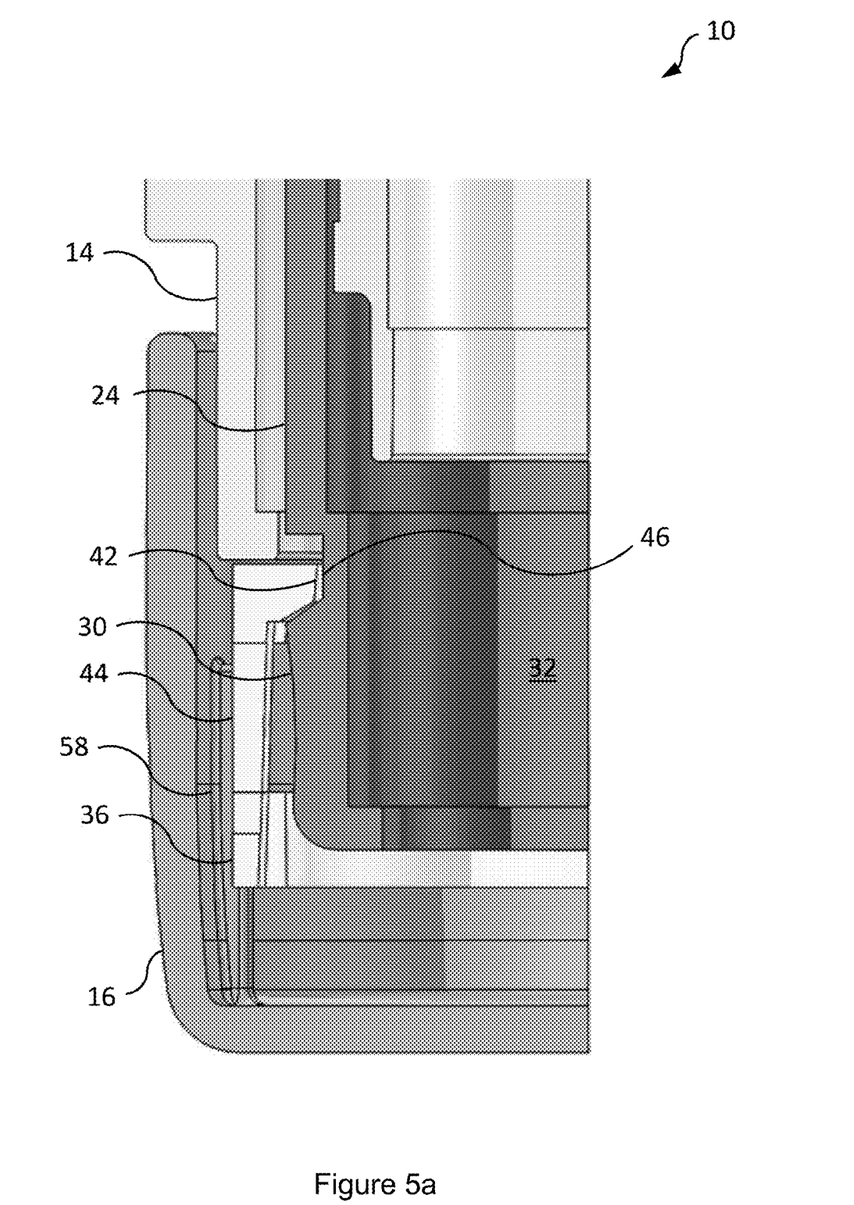
FIGS. 5A and 5B are partial cross-sectional views of the proximal end of the medicament delivery device of FIG. 1, in which the locking member is in a second axial position.
Figure 5B:
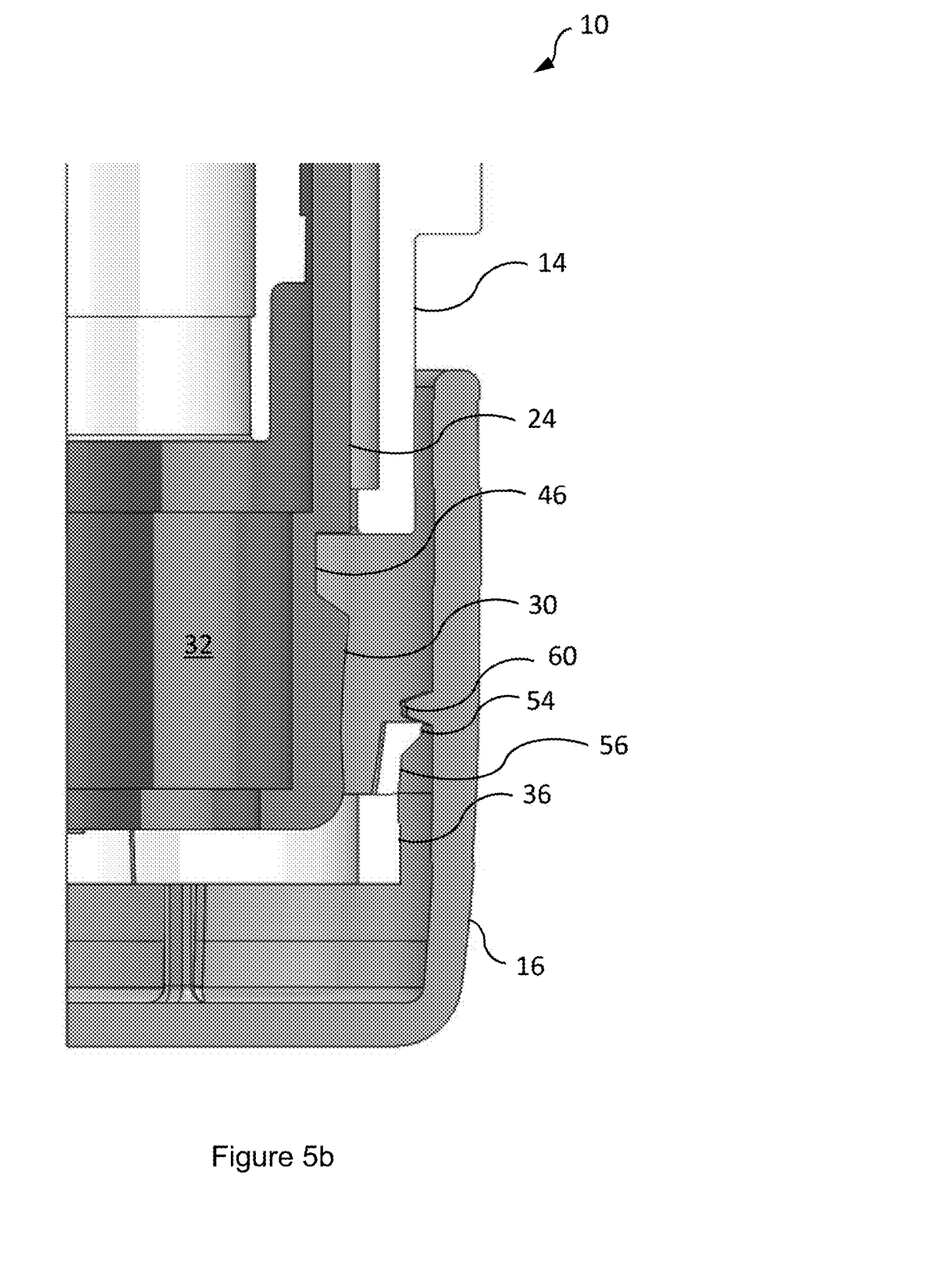

To ready the device 10 for use, a user may separate the second casing part 16 from the first casing part 14, for example by axially pulling the second casing part 16 away from the first casing part 14. In doing so, the locking member 36 may move axially relative to the second casing part 16, as the locking member 36 may remain engaged with the sleeve 24. Consequently, the locking member 36 may move to the second axial position. In the second axial position, the locking member 36 may be substantially non-deformed, as in the first axial position. In the second axial position, the locking member 36 may be receivable concentrically between the second casing part 16 and the outer wall 30, as shown in FIGS. 5A and 5B. As such, in the second axial position, the first and second casing parts 14, 16 may remain attached to one another, at least partially. In the second axial position, the locking member 36 may be disengageable from the outer surface 30. This is because, in the second axial position, the outward movement of the radially inward protrusions 42 may no longer be inhibited by abutment of the locking member 36 against the second casing part 16 (i.e. in the second axial position, there may be a space available radially outward of the locking member 36 to accommodate the radially outward movement of the radially outward protrusions 42). As such, in the second axial position, the first radially inwardly extending region 58 may have moved from an axial position in which the first radially inwardly extending region 58 is radially aligned with the radially inward protrusions 42 to an axial position in which the radially inwardly extending region 58 is not radially aligned with the radially inward protrusions 42.

Figure 6A:
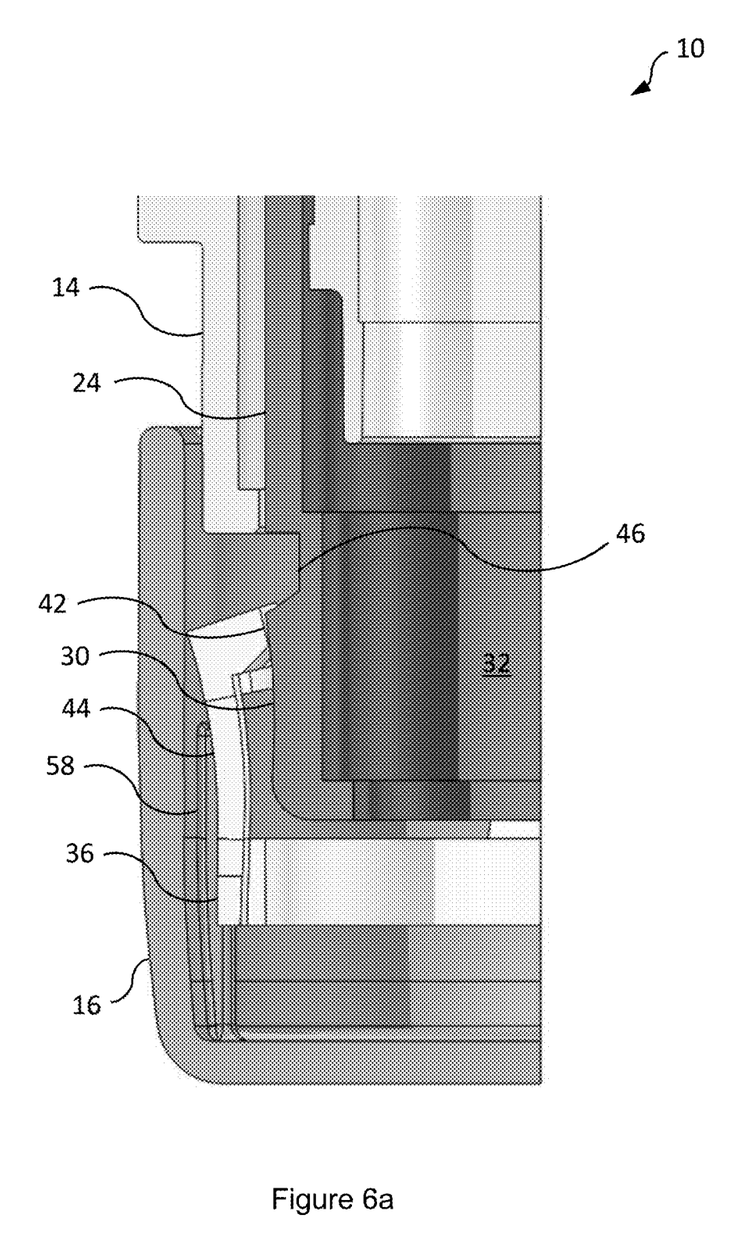
FIGS. 6A and 6B are partial cross-sectional views of the proximal end of the medicament delivery device of FIG. 1, in which the locking member is in the second axial position and the locking ring is deformed.
Figure 6B:
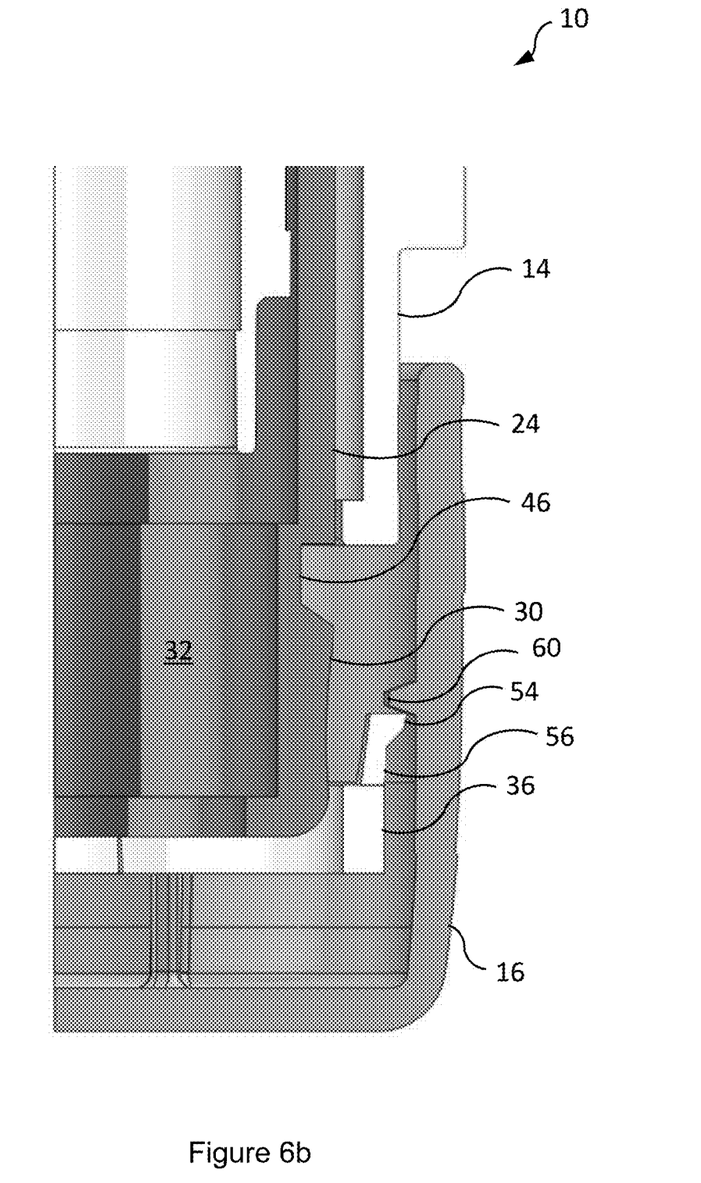

Continued axial movement of the locking member 36 relative to the second casing part 16 may be inhibited, as the radially outward protrusions 54 may be engageable with the second casing part 16 to retain the locking member 36 within the second casing part 16. More specifically, in the second axial position, the radially outward protrusions 54 may abut a second radially inwardly extending region 60 of the second casing part 16 to retain the locking member 36 within the second casing part 16. As shown in the illustrated embodiment, the second radially inwardly extending region 60 may be one or more ridges. Additionally, or alternatively, the second radially inwardly extending region 60 may comprise one or more ribs and/or one or more bumps. Continued axial movement may cause the radially inward protrusions to move radially outward, as shown in FIGS. 6A and 6B, which are offset by 90° to one another. This is because, in second axial position, the radially inward protrusions 42 may be deflected radially outward by abutment of the radially inward protrusions 42 against the outer surface 30. As shown in the illustrated embodiment, the radially inward protrusions 42 may be deflected radially outward by abutment against the groove 46, thus causing deformation of the first axially extending arms 44. As such, the locking member 36 may be disengageable from the outer surface 30 by separation of the first and second casing 14, 16 parts from one another. To facilitate deflection of the radially inward protrusions 42, either or both of the radially inward protrusions 42 and the outer surface 30 may comprise a chamfered surface.

Figure 7:
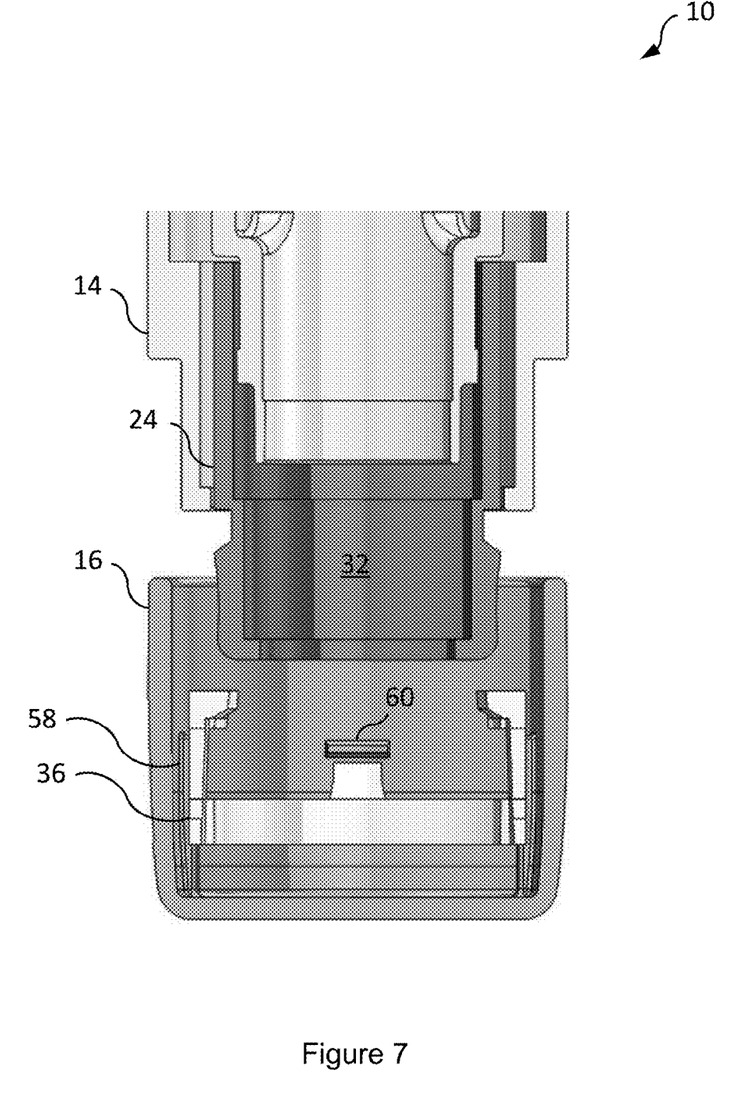
FIG. 7 is a partial cross-sectional view of the proximal end of the medicament delivery device of FIG. 1, in which first and second casing parts of the medicament delivery device are separated from one another.

FIG. 7 shows the first and second casing parts 14, 16 separated from one another and the locking member 36 retained in the second casing part 16. FIG. 7 shows the device 10 ready for use.

In certain embodiments, a removable needle sheath 62 may cover the needle 22 prior to use of the device 10. As such, the second casing part 16 may comprise a needle sheath remover 64 engageable with the needle sheath 62 such that the needle sheath 62 is removable from the needle 22 by separation of the first and second casing parts 14, 16 from one another. As the needle 22 may be receivable within the bore 32, so too may the needle sheath remover 64 be receivable within the bore 32. The needle sheath remover 64 may be receivable within the bore 32 via the open end 34.

As used herein, the terms "axial" and "axially" refer to an axis extending between the proximal and distal ends 18, 52 of the device 10. The terms "radial" and "radially" refer to a direction at least substantially perpendicular to and extending away from the axis.

Forward movement refers to a movement parallel to the axis and toward the proximal end 18 and rearward movement refers to a movement parallel to the axis and towards the distal end 52. As used herein, the term "proximal" refers to the end of the device 10 at which the needle 22 is located and/or attachable. As used herein, the term "distal" refers to the end of the device 10 furthest away from which the needle 22 is located and/or attachable. As used herein, the terms "include" and "comprise" are used synonymously, which terms and variants thereof are to be construed as non-limiting.

All of the features disclosed in this specification (including any accompanying claims and drawings) and/or all of the steps of any method or process so disclosed, may be combined in any combination, except combinations where at least some of such features and/or steps are mutually exclusive.

Each feature disclosed in this specification (including any accompanying claims and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims and drawings) or to any novel one, or any novel combination, of the steps of any method or process so disclosed. The claims should not be construed to cover merely the foregoing embodiments, but also any embodiments which fall within the scope of the claims.

The invention claimed is:

1. A medicament delivery device comprising:
   a housing for receiving a syringe, the housing having first and second casing parts
   separably attachable to one another, where the first casing has a terminal proximal end;
   a sleeve receivable within the housing and comprising a tubular wall having an open proximal end comprising a through hole, an inner surface delimiting a bore and an opposing outer surface comprising a groove, where the sleeve moves axially from a first position where the open proximal end extends proximally beyond the terminal proximal end to a second position where a needle extends out the through hole and proximally beyond the open proximal end; and
   a locking member receivable within the second casing part such that the locking member
   is axially movable between first and second axial positions relative to the second casing part, the
   locking member comprising a body portion having a radially inward protrusion extending therefrom such that in the first axial position radially inward protrusion is engaged with the groove to inhibit an axial movement of the sleeve from the first position to the second position and when in the second axial position the radially inward protrusion is disengaged from the groove.

2. The medicament delivery device according to claim 1, wherein the locking member is moveable from the first axial position to the second axial position by separation of the first and second casing parts from one another.

3. The medicament delivery device according to claim 2, wherein the locking member is engageable with the outer surface in that the outer surface has a radially inward groove extending therealong, in which the one or more radially inward protrusions is engageable.

4. The medicament delivery device according to claim 3, wherein the radially inward groove is circumferentially continuous.

5. The medicament delivery device according to claim 4, wherein the body portion has one or more first axially extending arms, proximate a free end of which a respective one of the one or more radially inward protrusions is integral or coupled to.

6. The medicament delivery device according to claim 5, wherein
   a plurality of the first axially extending arms are equispaced about the body portion.

7. The medicament delivery device according to claim 4, wherein the locking member is disengageable from the outer surface by a radially outward movement of the one or more radially inward protrusions.

8. The medicament delivery device according to claim 7, wherein
the radially outward movement of the one or more radially inward protrusions is by deformation
of the locking member.

9. The medicament delivery device according to claim 8, wherein the radially outward movement of the one or more radially inward protrusions is by deformation of the one or more first axially extending arms.

10. The medicament delivery device according to claim 9, wherein in the first axial position the radially outward movement of the one or more radially inward protrusions is inhibited by abutment of the locking member against the second casing part.

11. The medicament delivery device according to claim 10, wherein
in the radially outward movement of the one or more radially inward protrusions is inhibited by
abutment of the locking member against a first radially inwardly extending region of the second
casing part.

12. The medicament delivery device according to claim 11, wherein
the first radially inwardly extending region comprises one or more first bumps, ridges and/or ribs
extending over a first portion of the second casing part.

13. The medicament delivery device according to claim 12,
wherein in the first axial position the first radially inwardly extending region is radially aligned
with the one or more radially inward protrusions and in the second axial position the first radially
inwardly extending region is not radially aligned with the one or more radially inward protrusions.

14. The medicament delivery device according to claim 1, wherein the locking member is disengageable from the outer surface by separation of the first and second casing parts from one another.

15. The medicament delivery device according to claim 14, wherein the body portion has one or more radially outward protrusions extending therefrom engageable with the second casing part to retain the locking member within the second casing part.

16. The medicament delivery device according to claim 15, wherein
the body portion has one or more second axially extending arms, proximate a free end of which a respective one of the one or more radially outward protrusions is integral or coupled to.

17. The medicament delivery device according to claim 16,
wherein the one or more radially outward protrusions is engageable with the second casing part
by abutment of the one or more radially outward protrusions against a second radially inwardly
extending region of the second casing part.

18. The medicament delivery device according to claim 17, wherein
the second radially inwardly extending region comprises one or more second bumps, ridges
and/or ribs extending over a second portion of the second casing part.

19. The medicament delivery device according to claim 1, comprising a power source provided as one of a propellant or as a compression spring.

20. The medicament delivery device according to claim 19, wherein
the power source comprises a propellant that includes one of a hydrofluoroalkane ("HFA") or a
hydrofluoroolefin ("HFO").

21. A medicament delivery device comprising:
a housing for receiving a syringe, the housing having first and second casing parts
separably attachable to one another, where the first casing has a terminal proximal end;
a sleeve receivable within the housing and comprising a tubular wall having an open proximal end comprising a through hole, an inner surface delimiting a bore and an opposing outer surface, where the sleeve moves axially from a first position where the open proximal end extends proximally beyond the terminal proximal end to a second position where a needle extends out the through hole and proximally beyond the open proximal end; and
a locking member receivable within the second casing part such that the locking member
is axially movable between first and second axial positions relative to the second casing part, the
locking member comprising a body portion having a radially inward protrusion extending therefrom such that in the first axial position radially inward protrusion is engaged with the outer surface to inhibit an axial movement of the sleeve from the first position to the second position and when in the second axial position the radially inward protrusion is disengaged from the outer surface,
wherein when the locking member is in the first axial position a first radially inwardly extending region of the second casing part is radially aligned with the radially inward protrusion and when in the second axial position the first radially inwardly extending region is not radially aligned with the radially inward protrusion.

* * * * *